US00PP33702P2

(12) United States Plant Patent
McCracken

(10) Patent No.: US PP33,702 P2
(45) Date of Patent: Nov. 30, 2021

(54) ***RHODODENDRON* PLANT NAMED 'ROYAL RESILIENCE'**

(50) Latin Name: *Rhododendron catawbiense*
Varietal Denomination: Royal Resilience

(71) Applicant: Thomas Patrick McCracken, Zebulon, NC (US)

(72) Inventor: Thomas Patrick McCracken, Zebulon, NC (US)

( * ) Notice: Subject to any disclaimer, the term of this patent is extended or adjusted under 35 U.S.C. 154(b) by 0 days.

(21) Appl. No.: 17/208,194

(22) Filed: Mar. 22, 2021

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of hybrid *Rhododendron* plant named 'Royal Resilience' that is characterized by its fast and vigorous growing habit, its good growth in warm climates, and its very good resistance to powdery mildew and other foliar diseases.

2 Drawing Sheets

Botanical classification: *Rhododendron catawbiense.*
Cultivar designation: 'Royal Resilience'.

BACKGROUND OF THE INVENTION

The present invention relates to a new and distinct cultivar of *Rhododendron* plant of hybrid origin, botanically known as *Rhododendron catawbiense* 'Royal Resilience' and will be referred to hereafter by its cultivar name, 'Royal Resilience'. 'Royal Resilience' is a new cultivar of evergreen *Rhododendron* grown for use as a landscape plant.

The new cultivar was discovered in a large field that had been planted with plants produced by cuttings of *Rhododendron* 'Roseum Elegans' (not patented) by the Inventor in Raleigh, N.C. in spring of 1995. It is therefore presumed to be a branch mutation of 'Roseum Elegans'.

Asexual propagation of the new cultivar was first accomplished by softwood stem cuttings in Zebulon, N.C. in May of 1995 by the Inventor. Asexual propagation by softwood stem cuttings and tissue culture using meristematic tissue has determined that the characteristics of the new cultivar are stable and are reproduced true to type in successive generations.

SUMMARY OF THE INVENTION

The following traits have been repeatedly observed and represent the characteristics of 'Royal Resilience'. These attributes in combination distinguish 'Royal Resilience' as a new and distinct cultivar of *Rhododendron.*

1. 'Royal Resilience' exhibits a fast and vigorous growing habit.
2. 'Royal Resilience' exhibits good growth in warm climates.
3. 'Royal Resilience' exhibits very good resistance to powdery mildew and other foliar diseases.

The parent of 'Royal Resilience' is similar to 'Royal Resilience' in flower color, growth habit and blooming time.

The parent of 'Royal Resilience' differs from 'Royal Resilience' in having less resistance to powdery mildew and other foliar diseases. 'Royal Resilience' can also be most closely compared to the *Rhododendron* cultivar 'English Roseum' (not patented). 'English Roseum' is similar to 'Royal Resilience' in growth habit. 'English Roseum' differs from 'Royal Resilience' in having flowers that are more lavender in color.

BRIEF DESCRIPTION OF THE DRAWINGS

The accompanying color photographs were taken of a 15-year-old plant of the new cultivar as grown outdoors in a nursery plot in Zebulon, N.C.

The photograph in FIG. 1 provides a view of 'Royal Resilience' in bloom.

Figure 1:
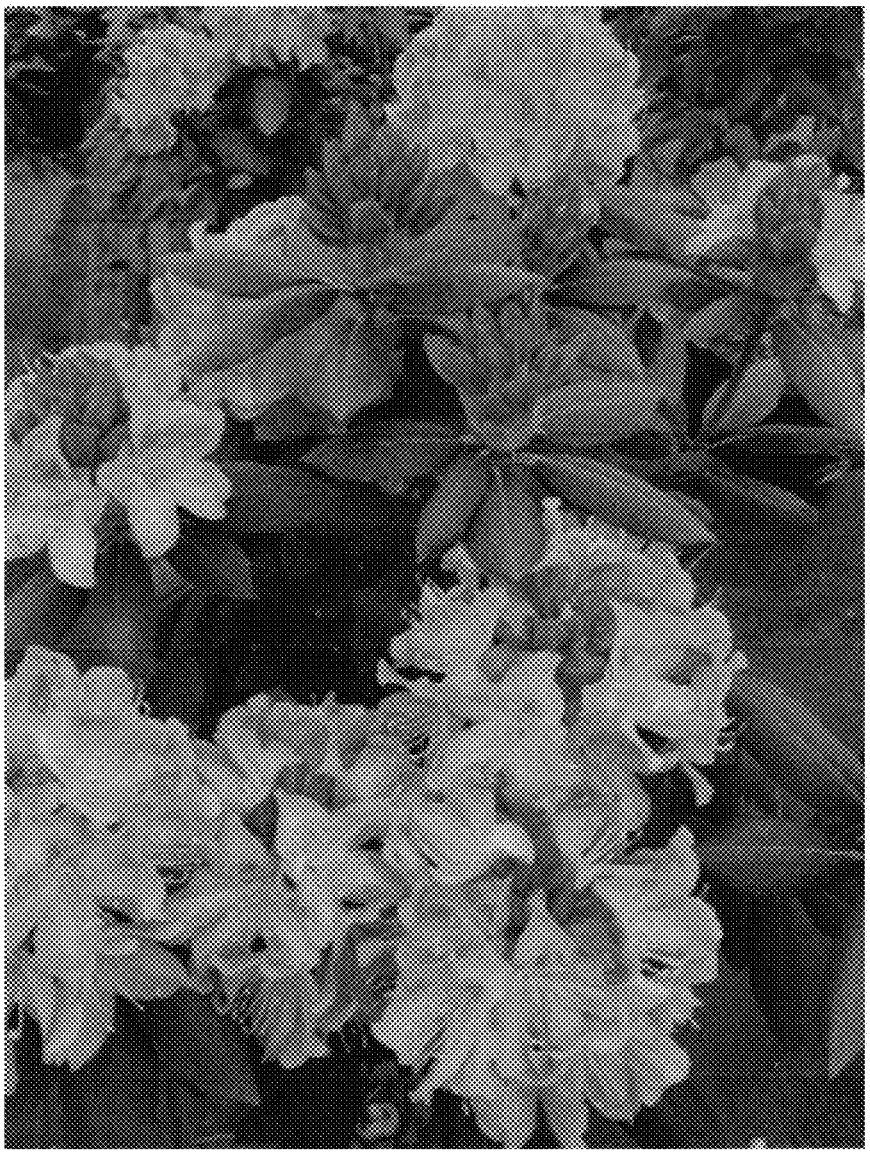
Figure 2:
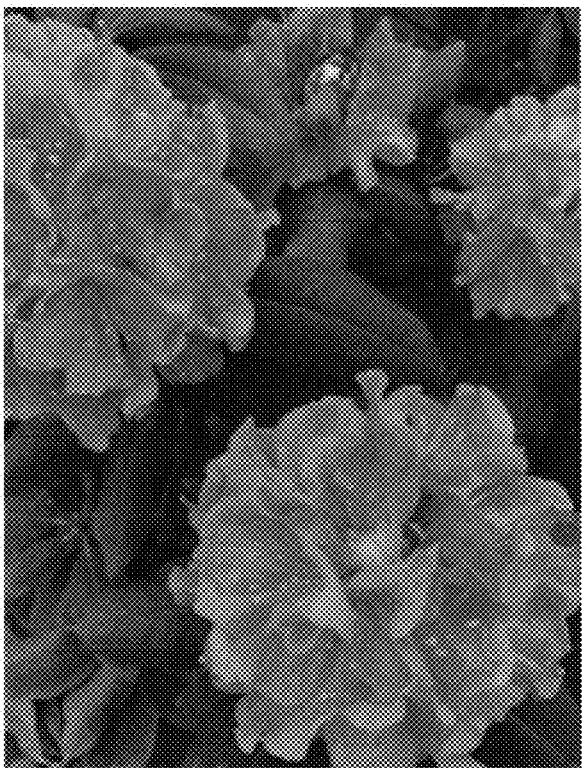

The photograph in FIG. 2 provides a close-up view of a fully open inflorescence of 'Royal Resilience'.

Figure 3:
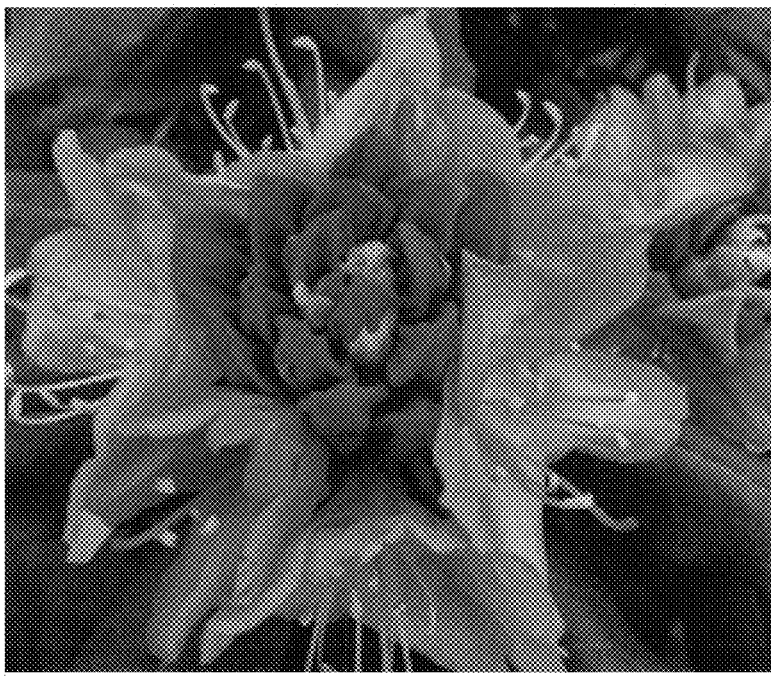

The photograph in FIG. 3 provides a close-up view of a partially open inflorescence of 'Royal Resilience'.

The colors in the photographs are as close as possible with the digital photography and printing techniques utilized and the color codes in the detailed botanical description accurately describe the new *Rhododendron.*

DETAILED BOTANICAL DESCRIPTION OF THE PLANT

The following is a detailed description of 15-year-old plants of the new cultivar as grown outdoors in a nursery plot in Zebulon, N.C. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period.*—April in Raleigh, N.C.

*Plant type.*—Evergreen shrub.

*Plant habit.*—Compact, irregularly-rounded, and densely branched.

*Height and spread.*—Plants 15 years in age as grown in the landscape average of 2.4 m in height and spread.

*Hardiness.*—U.S.D.A. Zones 4 to 8.

*Diseases and pests.*—High tolerance to powdery mildew (caused by *Erysiphe azalea*) and other foliar and root diseases typically caused by *Ovulinia azalea* and *Phytophthora* sp. however specific resistant causative agents have not been identified.

*Root description.*—Fibrous and 165A in color.

*Propagation.*—Tissue culture (preferred) or softwood stem cuttings.

*Root development.*—4 weeks to initiate roots and an average of 4 to 6 months to produce a young plant from a rooted cutting.

*Growth rate.*—Vigorous.

Stem description:

*Shape.*—Round.

*Stem color.*—Young growth; 144A, mature wood; 165A with vertical fissures 165C.

*Stem size.*—Main stems; an average of 36 cm in length and 6.5 mm in width, lateral branches; 17 cm in length and 6 mm in width.

*Stem surface.*—Young growth; slightly rough to the touch, glabrous, with lenticels; an average of 6 per sq. cm, an average of 1 mm in length and 166A in color, mature wood; moderately rough-barked with vertical fissures and dull.

*Stem aspect.*—Lateral stems held an average of 45° to the main stems.

*Stem strength.*—Strong.

*Branching.*—Densely branched.

Foliage description:

*Leaf shape.*—Elliptic.

*Leaf division.*—Simple.

*Leaf base.*—Rounded to cuneate.

*Leaf apex.*—Acuminate.

*Leaf venation.*—Pinnate, upper surface midrib 144A in color with lateral vein color matching leaf coloration, lower surface midrib 145C, lateral veins 138C.

*Leaf margins.*—Entire.

*Leaf attachment.*—Petiolate.

*Leaf arrangement.*—Whorled.

*Leaf internode length.*—2 to 5 mm.

*Leaf orientation.*—Held slightly upright to horizontal.

*Leaf aspect.*—Slightly cupped (convex).

*Leaf surface.*—Upper surface; smooth, glabrous, satiny with a thick texture, lower surface; smooth, glabrous, dull.

*Leaf color.*—Young leaves upper surface; 147A, young leaves lower surface; 147C, mature and fall leaves upper surface; slightly darker than 147A, mature and fall leaves lower surface; a color between 147B and 147C.

*Leaf size.*—Mature to an average of 10 cm in length and 5 cm in width.

*Leaf quantity.*—An average of 6 leaves per branch 7 cm in length.

*Petioles.*—Average of 2.2 mm in length and 3 mm in diameter, rounded on lower surface and flat on upper surface, very strong, 138B in color, surface glabrous and leathery.

Flower description:

*Inflorescence type.*—Raceme.

*Lastingness of flowers.*—An average 9 days, mostly self-cleaning.

*Inflorescence size.*—Average of 10 cm in height and 12 cm in width.

*Flower size.*—An average of 4 cm in depth and 6.2 cm in diameter.

*Flower fragrance.*—Slightly sweet.

*Flower shape.*—Broad tubular funnel.

*Flower number.*—An average of 14 per inflorescence.

*Flower aspect.*—Upright and outward.

*Flower bud.*—Obovate in shape, pointed apex, an average of 3.8 cm in length and 1.8 cm in diameter, color; a blend of 72A and N81A and blending into 75A and 75B at base, glabrous and slightly satiny surface.

*Flower attachment.*—Pedicel.

*Petal number.*—5.

*Petal shape.*—Elliptic.

*Petal aspect.*—Upward and spreading with apex slightly reflexed.

*Petal color.*—Upper surface when opening; a blend of 77B and 77C with margins suffused with 77A and petal spots on one petal 165A, lower surface when opening: a blend of 72A, 72B, and N81A and blending into 75A and 75B at base, upper surface when fully open; a blend of 77C and 77D with margins suffused with 77B and petal spots on one petal 165B, lower surface when fully open; a blend of 77B, 77C, and 77C and blending into 75C and 75D at base, petals drop without fading.

*Petal surface.*—Glabrous on upper and lower surface.

*Petal margins.*—Entire and slightly undulate.

*Petal apex.*—Rounded with small notch at tip.

*Petal base.*—Lower 30 to 50% fused.

*Petal size.*—Average of 4.4 cm in length and 2.6 cm in width.

*Sepal number.*—5.

*Sepal shape.*—Broadly ovate.

*Sepal margin.*—Entire.

*Sepal size.*—Average of 1 mm in length and 1.5 mm in width.

*Sepal arrangement.*—Forming a shallow cup around corolla tube base.

*Sepal surface.*—Glabrous on upper and lower surface.

*Sepal apex.*—Rounded to broadly acute.

*Sepal base.*—Fused.

*Sepal color.*—Immature and mature upper surface; 145A, immature and mature lower surface; 161D.

*Calyx.*—Shallow cup shape, an average of 1 mm in length and 4 mm in diameter.

*Peduncle.*—An average of 4 cm in length and 5 mm in width, pedicels implanted in a whorled arrangement, strong, N144C in color, glabrous surface.

*Pedicels.*—An average of 3 cm in length and 2 mm in diameter, smooth and glabrous surface, strong, N144A in color.

*Inflorescence bracts.*—An average of 12, imbricate, located at base of inflorescence, elliptic in shape, concave, surface glabrous and satiny on both surfaces, entire margin, apiculate apex, truncate base, upper and lower surface a blend of 144A and 144D in color with base 166C.

Reproductive organs:

*Gynoecium.*—1 Pistil, 4 cm in length, stigmas; circular, convex, and dome-shaped, 68B and N199D in color, style; an average of 4 cm in length and 1 mm in width, 68B in color, ovary; superior, oblong in shape, 5 mm in length, and 146B in color and suffused at apex with 68A.

*Androecium.*—Stamens; average of 10, anthers; oblong to elliptical in shape, 4 mm in length and 1.5 mm in width, 168D in color; pollen is moderate in quantity and 158B in color.

*Fruit/seeds.*—None observed.

It is claimed:

1. A new and distinct cultivar of *Rhododendron* plant named 'Royal Resilience' as herein illustrated and described.

* * * * *